United States Patent [19]

Steffen et al.

[11] 4,158,707

[45] Jun. 19, 1979

[54] PARENTERAL PREPARATIONS

[75] Inventors: Hans Steffen, Arisdorf; Dieter Schmidt, Basel, both of Switzerland

[73] Assignee: Hoffmann-La Roche Inc., Nutley, N.J.

[21] Appl. No.: 813,913

[22] Filed: Jul. 8, 1977

[51] Int. Cl.² ................ A61K 31/33; A61K 47/00
[52] U.S. Cl. ................................ 424/244; 424/365
[58] Field of Search ........................ 424/38, 244

[56] References Cited

U.S. PATENT DOCUMENTS

| | | | |
|---|---|---|---|
| 3,044,931 | 7/1962 | Geigy | 424/365 |
| 3,197,368 | 7/1965 | Loppe et al. | 424/365 |
| 3,714,352 | 1/1973 | Davis et al. | 424/243 |
| 3,900,561 | 8/1975 | Davis et al. | 424/243 |
| 3,917,830 | 11/1975 | Davis et al. | 424/243 |
| 4,005,190 | 1/1977 | Mader et al. | 424/127 |
| 4,017,616 | 4/1977 | Gomez | 424/244 |

FOREIGN PATENT DOCUMENTS 706607 3/1954 United Kingdom.

OTHER PUBLICATIONS

Arch. Intern. Med., vol. 130, Oct. 1972, pp. 506–527.
Remingtons Pharm. Sci. 15th Ed., 1975, Mack Publishing Co., Easton Pa. pp. 316–321, 333, 425, 736, 737 & 1008–1012.

*Primary Examiner*—Donald B. Moyer
*Attorney, Agent, or Firm*—Jon S. Saxe; George M. Gould; R. Hain Swope

[57] ABSTRACT

Aqueous vehicles for insoluble or sparingly soluble medicaments suitable for parenteral administration are disclosed. The subject vehicles contain, in addition to pharmaceutical adjunct materials to render them isotonic, preserve them and the like, a micelle forming agent comprising cholic acid or a derivative thereof in combination with a lipoid.

7 Claims, No Drawings

PARENTERAL PREPARATIONS

BACKGROUND OF THE INVENTION

The present invention is directed to aqueous vehicles suitable for the parenteral administration of medicaments which are insoluble or only slightly soluble in water and pharmaceutical preparations incorporating such vehicles.

Vehicles known in the art for rendering insoluble or sparingly soluble medicaments suitable for parenteral administration utilize, generally, one or a mixture of synthetic solubilizing agents such as, for example, propylene glycol, polyethylene glycols, various emulsifying agents such as, for example, those marketed under the tradenames Cremophor EL, the Tweens and the Pluronics. The latter group of solubilizing agents functions by the formation of a colloidal system (micelles). The synthetic solubilizing agents including the above-mentioned micelle forming agents can be disadvantageous in that, upon parenteral administration, they may cause side effects such as, for example, allergic reactions, anaphylactic shock, hemolysis and pyrogenic action.

In addition to the synthetic micelle forming agents discussed above, there are available to the pharmaceutical compounder natural micelle forming agents such as, for example, cholic acid and various derivatives thereof. These natural micelle forming agents are, however, ionic and, therefore, strongly lytic. They produce hemolysis and have accordingly not previously been considered for compounding of preparations for parenteral administration.

It has been found in accordance with the present invention that the disadvantageous lytic action of the above-mentioned cholic acid derivatives can be substantially reduced or even eliminated by combining such micelle forming agents with certain lipoids. There is thus realized parenteral vehicles for insoluble or sparingly soluble medicaments which utilize as a micelle forming agent cholic acid and certain derivatives thereof not heretofore considered for use in parenteral preparations.

DETAILED DESCRIPTION OF THE INVENTION

The present invention is directed to aqueous vehicles suitable for the parenteral administration of insoluble or sparingly soluble medicaments, a process of preparing same and pharmaceutical preparations incorporating such vehicles. The subject vehicle contains, as the micelle forming agent, cholic acid or a derivative thereof in combination with a lipoid. The vehicle also contains suitable pharmaceutical adjuncts to make it isotonic as well as preservatives and the like and may of course contain additional medicaments which are soluble in water.

The micelle forming agents utilized in the parenteral vehicles of the subject invention comprise cholic acid derivatives represented by the general formula

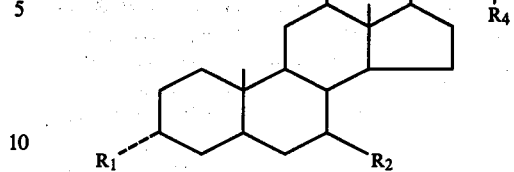

wherein $R_1$, $R_2$ and $R_3$ are hydrogen, hydroxy or an exocyclic keto group and $R_4$ is carboxy group or the radical $-CO-NH-(CH_2)_n-R$ wherein n is 1 or 2 and R is $-COOH$ or $-SO_3H$ derivatives thereof containing one or two double bonds in the steroid skeleton, or pharmaceutically acceptable salts thereof.

Wherein the compounds of formula I contain one or two double bonds in the steroid skeleton, such bonds may be at position -7, position -11 or position -9.

Preferred substances of formula I are the dihydroxy cholic acids, i.e. two members of $R_1$–$R_3$ are hydroxy. Among such compounds are the following: deoxycholic acid ($R_1$ and $R_3$ are hydroxy, $R_2$ is hydrogen and $R_4$ is carboxyl); glycodeoxycholic acid ($R_1$ and $R_3$ are hydroxy, $R_2$ is hydrogen and $R_4$ is the radical $-CO-NH-CH_2-COOH$); taurodeoxycholic acid ($R_1$ and $R_3$ are hydroxy, $R_3$ is hydrogen and $R_4$ is the radical $-CO-NH-CH_2-CH_2-SO_3H$); chenodeoxycholic acid ($R_1$ and $R_2$ are hydroxy, $R_3$ is hydrogen and $R_4$ is carboxyl); glycochenodeoxycholic acid ($R_1$ and $R_2$ are hydroxy, $R_3$ is hydrogen and $R_4$ is the radical $-CO-NH-CH_2-COOH$); and taurochenodeoxycholic acid ($R_1$ and $R_2$ are hydroxy, $R_3$ is hydrogen and $R_4$ is the radical $-CO-NH-CH_2-CH_2-SO_3H$).

Particularly preferred micelle forming agents of formula I in accordance with the present invention are the trihydroxy cholic acids, i.e. $R_1$–$R_3$ are hydroxy. Among such compounds are the following: cholic acid ($R_4$ is carboxyl); glycocholic acid ($R_4$ is the radical $-CO-NH-CH_2-COOH$) and taurocholic acid ($R_4$ is the radical $-CO-NH-CH_2-CH_2-SO_3H$).

The salts of the compounds of formula I are salts with pharmaceutically acceptable bases, preferably alkali metal salts and most preferably the sodium salt.

The lipoids which are combined with the compounds of formula I in accordance with the present invention are pharmaceutically acceptable lipoids which are recognized as being suitable for parenteral administration such as, for example, phosphatidylcholines, glycerin ether phosphatides, phosphatidylethanolamines, phosphatidylinositol, phosphatidylserines, sphinomyelin, plasmalogens, cardiolipin, sulfatides and monoglycerides. Preferred lipoids are the phosphatides, particularly the phosphatidylcholines.

The ratio between the micelle forming agent of formula I and the lipoid component can vary within a rather wide range. It is preferred, however, in accordance with the present invention to utilize the micelle forming agent of formula I and the lipoid in a ratio of between about 0.1:1 to about 2:1. A particularly preferred ratio of a compound of formula I to lipoid is from about 0.8:1 to about 1.5 to 1.

The amount of the combination of micelle forming agent of formula I and lipoid present in a pharmaceutical preparation suitable for parenteral administration prepared according to the present invention can also vary within rather wide limits. It is preferred, however, that such combination be present in the final preparation in between about 50 mg to about 300 mg per milliliter.

The amount of insoluble or sparingly soluble medicament in a parenteral preparation utilizing the novel vehicles described herein can also vary within rather wide limits. Preferably, however, such preparations contain from about 0.1 to about 20 mg/ml of the final preparation.

The medicaments insoluble or sparingly soluble which can be prepared for parenteral administration utilizing the vehicle of the subject invention include, for example, the benzodiazepines such as diazepam, clonazepam, flunitrazepam, nitrazepam, medazepam, bromazepam and the like, vitamin A derivatives, vitamin K derivatives, particularly vitamin $K_1$. The vehicle of the subject invention may likewise be utilized to prepare injectable compositions containing, for example, certain neutroleptic agents, antidepressives, antiinfectives and steroids which are insoluble or only sparingly soluble in water. A parenteral preparation containing the novel vehicle of the invention may contain more than one of such medicaments. In addition, the parenteral preparations contemplated herein can also contain one or more water-soluble medicaments as well as soluble pharmaceutically acceptable adjunct materials such as buffers, additives to render the preparation isotonic, preservatives and the like.

The parenteral preparations of the present invention, as is commonly the case with such preparations, must be adjusted to be isotonic with blood. Suitable additives which could be utilized for this purpose include, for example, physiological sodium chloride and glucose solution, Tris buffer, phosphate, citrate and glycine buffers, citrate-phosphate mixed buffer and the like. The osmotic pressure of the instant parenteral preparations should also approximate that of blood, i.e. about 300 mOsm, but can vary within certain limits.

The pharmaceutical preparations for parenteral administration in accordance with the present invention can be prepared by simple admixture of the components as discussed herein. It is preferred, however, to dissolve the lipoid, the micelle forming agent and the medicament in a suitable organic solvent in which they are soluble, preferably a lower alkanol such as, for example, methanol or ethanol. The organic solvent would then be driven off and the water, isotonizing additive and other additives or soluble medicaments would then be added, preferably as a mixture.

In a more preferred process according to the present invention, about one molar part of micelle forming agent, about one molar part lipoid, from about 50 to about 250 molar parts water and one or more insoluble or sparingly soluble medicaments are stirred vigorously until homogeneous. It is possible to carry out this procedure with the addition of up to about 2% by weight, based on the weight of the other components, of an organic solvent such as described above, most preferably ethanol. When the mixture is homogeneous, the desired amount of water, isotonizing additive and other water-soluble additives, if desired, are incorporated. In principle, the micellar solution can initially be prepared and the insoluble or sparingly soluble medicament solubilized therein.

The time required to form the homogeneous mixture in accordance with the present invention will vary with the nature of the micelle forming agent, the lipoid component and the medicament. In most instances this time can be reduced by warming the mixture for a short period.

Wherein the medicament in the novel parenteral compositions of the subject invention is light or oxygen sensitive, it is necessary to prepare and package the subject preparations with the exclusion of light and/or under an inert atmosphere, e.g. nitrogen. In the latter case it is preferred to add an effective amount of a antioxidant such as, for example, sodium ascorbate, sodium hydrogen bisulfide, sodium pyrosulfite or the like to the final injectable composition.

The compositions for parenteral administration prepared in accordance with the present invention are miscible with plasma and conventional infusion solutions, e.g. isotonic glucose or sodium chloride. The subject injectable compositions have also demonstrated rapid release of the insoluble or sparingly soluble medicament. Further, the vehicle formulations of the subject invention have demonstrated very low toxicity.

The following examples further illustrate the invention. Unless otherwise indicated, all temperatures are in degrees Centigrade.

EXAMPLE 1

A total of 3 g of egg lecithin (isolated according to Singleton et al., J. Am. Oil. Chem. Soc. 42 (1965) 53), 2 g of sodium glycocholate and 150 mg of diazepam were dissolved in a round flask in 150 ml of ethanol treated with nitrogen. The ethanol was then evaporated in a rotary evaporator under vacuum at 35° thus forming a lipid film in the flask. 25 ml of 1/15-M phosphate buffer solution (pH 7) treated with nitrogen were added under nitrogen atmosphere. The micelles formed spontaneously at room temperature. 300 mg of sodium ascorbate powder were added and dissolved. The resulting solution was filtered sterile under laminar flow conditions and filled into ampules containing nitrogen which were sealed. During the entire procedure contact with air was avoided, in order to obtain an oxygen-free solution in the ampule.

EXAMPLE 2

A total of 2.9 of egg lecithin, 2 g of sodium taurocholate and 150 mg of diazepam were dissolved in a round flask in 150 ml of ethanol treated with nitrogen. An injection preparation was formed from the resulting solution according to the method of Example 1.

EXAMPLE 3

A total of 40 mg of sodium glycocholate was dissolved in 1 ml of 1/15-M phosphate buffer. To this solution was added 61.6 mg of egg lecithin and stirring was continued until the solution was clear (approximately 2 days). 10 mg of diazepam were stirred into the resulting solution. Stirring was continued for 12 hours after which the solution was allowed to settle. The supernatant containing mixed micelles having a diazepam concentration of 2 mg/ml was removed and packaged in accordance with Example 1.

EXAMPLE 4

Injectable preparations were formed according to the procedure of Example 3 replacing the egg lecithin with 62.2 mg of phosphatidylinositol.

EXAMPLE 5

Injectable preparations were formed according to the procedure of Example 3 replacing the egg lecithin with 65.4 mg of phosphatidylserine.

EXAMPLE 6

Injectable preparations were formed according to the procedure of Example 3 replacing the egg lecithin with 60.6 mg of sphingomyelin.

EXAMPLE 7

Injectable preparations were formed according to the procedure of Example 3 replacing the egg lecithin with 61.6 mg of sulphatide (bovine).

EXAMPLE 8

Injectable preparations were formed according to the procedure of Example 3 replacing the egg lecithin with 57.2 mg of dimyristoyl lecithin.

EXAMPLE 9

Injectable preparations were formed according to the procedure of Example 3 replacing the egg lecithin with 11.8 mg of cardiolipin and utilizing only 20 mg of sodium glycocholate.

EXAMPLE 10

A mixture of 75 mg of egg lecithin and 48.7 mg of sodium glycocholate were dissolved in ½ ml of methanol. The methanol was evaporated in a rotary evaporator at 35° under vacuum. 1 ml of 1/15-M phosphate buffer was then added and 5 mg of diazepam were stirred into the resulting mixture. Stirring was continued for 12 hours at room temperature, after which the solution was allowed to settle. The supernatant containing mixed micelles having a diazepam concentration of 2.2 mg/ml was removed and packaged in accordance with Example 1.

EXAMPLE 11

A total of 5.58 g of glycocholic acid, 1.2 ml of 10-M sodium hydroxide solution and 24.4 ml of 1/15-M phosphate buffer (treated with nitrogen; oxygen free and potassium free) were shaken until a solution was formed. 9.6 g of soya lecithin, 200 mg of diazepam and 600 mg of sodium ascorbate were added and the mixture shaken and stirred until a homogeneous, honey-like phase was formed. An additional 20 ml of oxygen-free phosphate buffer were then added. A yellowish clear solution was formed which was filtered sterile and filled into ampules.

EXAMPLE 12

A total of 390 mg of sodium glycocholate were dissolved in 1.2 ml of water. 605 mg of soya lecithin and 100 mg of vitamin $K_1$ were added and the mixture intensively stirred until it was homogeneous. The highly viscous solution became clear after about 18 hours. The solution was diluted with 10 ml of 1/15-M phosphate buffer.

EXAMPLE 13

The procedure of Example 12 was followed, but with the addition of 2% ethanol. The highly viscous solution became clear more quickly than that formed in Example 12.

We claim:

1. An aqueous pharmaceutical preparation suitable for parenteral administration comprising a benzodiazepine, a phosphatide and a micelle forming agent selected from the group consisting of cholic acid, deoxycholic acid, glycodeoxycholic acid, taurodeoxycholic acid, chenocleoxycholic acid, glycochenodeoxycholic acid, taurochenodeoxycholic acid, glycocholic acid, taurocholic acid and pharmaecutically acceptable salts thereof.

2. A preparation in accordance with claim 1 additionally containing an isotonic effective amount of a suitable pharmaceutical isotonizing agent.

3. A preparation in accordance with claim 1 wherein said micelle forming agent is selected from the group consisting of cholic acid, glycocholic acid and taurocholic acid.

4. A preparation in accordance with claim 1 wherein said phosphatide in a phosphatidylcholine.

5. A preparation in accordance with claim 1 wherein the ratio between said micelle forming agent and said lipoid is between from about 0.1:1 to about 2:1.

6. A preparation in accordance with claim 5 wherein the ratio between said micelle forming agent and said lipoid is between from about 0.8:1 to about 1.5:1.

7. A preparation in accordance with claim 1 wherein said micelle forming agent is glycocholic acid.

* * * * *

UNITED STATES PATENT AND TRADEMARK OFFICE
CERTIFICATE OF CORRECTION

PATENT NO. : 4,158,707
DATED : June 19, 1979
INVENTOR(S) : HANS STEFFEN and DIETER SCHMIDT It is certified that error appears in the above-identified patent and that said Letters Patent are hereby corrected as shown below:

Please insert on cover page of patent, left-hand column, between section [22] and section [51] the following:

[30] Foreign Application Priority Data

July 12, 1976    Austria ................A 5111/76

June 7, 1977    Switzerland.............. 6994/77

Signed and Sealed this

Twenty-second Day of March 1983

[SEAL]

Attest:

GERALD J. MOSSINGHOFF

Attesting Officer

Commissioner of Patents and Trademarks